United States Patent [19]
McClure et al.

[11] Patent Number: 5,864,384
[45] Date of Patent: Jan. 26, 1999

[54] VISUAL FIELD TESTING METHOD AND APPARATUS USING VIRTUAL REALITY

[76] Inventors: Richard J. McClure, 4981 September St., San Diego, Calif. 92110; R. Kemp Massengill, 664 Hymettus Ave., Leucadia, Calif. 92024

[21] Appl. No.: 700,754

[22] Filed: Jul. 31, 1996

[51] Int. Cl.⁶ ........................................ A61B 3/02
[52] U.S. Cl. ........................... 351/224; 351/226
[58] Field of Search .................... 351/200, 209, 351/210, 222, 224, 245, 246, 226

[56] References Cited

U.S. PATENT DOCUMENTS

| | | | |
|---|---|---|---|
| 3,983,474 | 9/1976 | Kuipers | 324/43 R |
| 4,205,224 | 5/1980 | Mecklenborg | 250/201 |
| 4,634,243 | 1/1987 | Massof et al. | 351/243 |
| 4,848,898 | 7/1989 | Massof | 351/242 |
| 4,896,962 | 1/1990 | Menn et al. | 356/152 |
| 4,897,511 | 1/1990 | Itaya et al. | 128/18 |
| 4,956,794 | 9/1990 | Zeevi et al. | 364/559 |
| 5,113,177 | 5/1992 | Cohen | 340/705 |
| 5,151,722 | 9/1992 | Massof et al. | 351/158 |
| 5,231,430 | 7/1993 | Kohayakawa et al. | 351/243 |
| 5,237,351 | 8/1993 | Kohayakawa et al. | 351/243 |
| 5,308,246 | 5/1994 | Balocco | 434/262 |
| 5,384,580 | 1/1995 | Kadota | 345/145 |
| 5,386,216 | 1/1995 | Iino | 345/7 |
| 5,394,517 | 2/1995 | Kalawsky | 395/129 |
| 5,398,039 | 3/1995 | Furuya et al. | 345/7 |
| 5,400,155 | 3/1995 | Ueda et al. | 359/9 |
| 5,414,439 | 5/1995 | Groves et al. | 345/7 |
| 5,442,456 | 8/1995 | Hansen | 358/342 |
| 5,461,435 | 10/1995 | Rootzen et al. | 351/224 |
| 5,461,436 | 10/1995 | Campbell | 351/242 |
| 5,478,239 | 12/1995 | Fuerst et al. | 434/247 |
| 5,483,305 | 1/1996 | Kohayakawa | 351/243 |
| 5,488,508 | 1/1996 | Haseltine | 359/362 |
| 5,550,602 | 8/1996 | Braeuning | 351/243 |
| 5,565,949 | 10/1996 | Kasha, Jr. | 351/224 |

FOREIGN PATENT DOCUMENTS 0 428 604  5/1991  European Pat. Off. .
WO 96/14793  5/1996  WIPO .

OTHER PUBLICATIONS

Arnst, C.; *Eyeing Glaucoma in Virtual Reality*; Business Week; Jun. 30, 1997; p. 92.

Bethke, W.; *Glaucoma Screening to Go*; Review of Ophthalmology; Jul., 1997; p. 21.

Welch Allyn advertisement; Review of Ophthalmology; Jul., 1997; 4 un–numbered pages.

Abelson, Mark; "Glaucoma Management"; pp. 160–161; from *Review of Ophthalmology*; Oct./1996; Chilton Publications; Radnor, Pennsylvania.

American Academy of Ophthalmology; "Final Program: Centennial Meeting of the American Academy of Ophthalmology"; held Oct. 27–31, 1996, Chicago, Illinois; pp. 192–193; 1996; American Academy of Opthalmology; San Francisco, California.

Andre, A. D., et al.; "Visual Scanning in the Functional Visual Field"; pp. 114–117; from *SID International Symposium Digest of Technical Papers*; 1993; Society for Information Display; Playa del Rey, California.

(List continued on next page.)

*Primary Examiner*—Huy Mai

[57] ABSTRACT

A method and apparatus are disclosed for using Virtual Reality for testing and quantifying visual information from the eye, the visual pathways, and the brain. Head-gear configuration allows the patient to observe a field of view into which sequenced test stimuli are presented by an excitation device commanded by a computer. Interactive sensory feedback both to and from the patient enables computer-driven presentation and modulation of test stimuli to measure with precision such parameters as visual field performance, visual acuity, and color vision. Using the system allows the patient unprecedented freedom of movement of the head and body, thus minimizing or even eliminating the stress and fatigue common with conventional non-Virtual Reality visual field testing systems.

94 Claims, 1 Drawing Sheet

OTHER PUBLICATIONS

Arditi, A., et al.; "Visualization of 2–D and 3–D Aspects of Human Binocular Vision"; pp. 643–646; from *SID Internation Symposium Digest of Technical Papers*; 1992; Society for Information Display; Playa del Rey, California.

Ayache, N., et. al; "Steps Toward the Automatic Interpretation of 3D Images"; pp. 107–120; from *3D Imaging in Medicine: Algorithms, Systems, Applications*; edited by Karl Heinz Hohne, Henry Fuchs, and Steven M. Pizer; 1990; NATO Scientific Affairs Division and Springer–Verlag; Berlin, Germany.

Bancroft, G., et. al.; "Tools for 3D Scientific Visualization in Computational Aerodynamics at NASA Ames Research Center"; pp. 161–172; from *Three Dimensional Visualization and Display Technologies, Proceedings of the SPIE—The International Society of Optical Engineering*, edited by W.E. Robbins and S.S. Fisher; 1989; SPIE; Bellingham, Washington.

Barfield, W., et. al.; "Spatial Situational Awareness as a Function of Frame of Reference, Virtual Eyepoint Elevation, and Geometric Field of View", pp. 107–110; from *SID International Symposium Digest of Technical Papers*; 1993; Society for Information Display; Playa del Rey, California.

Benedikt, Michael; "Cyberspace: Some Proposals"; pp. 132–168; from *Cyberspace: First Steps*; edited by Michael Benedikt; 1991 (Seventh Printing: 1994); Massachusetts Institute of Technology; Cambridge, Massachusetts.

Bertol, Daniela; "Architecture of Images: An Investigation of Architectural Representations and the Visual Perception of Three–Dimensional Space"; pp. 87–94; from *Leonardo*, vol. 29, No. 2; Copyright 1996; ISAST, U.S.A.

Bricken, Meredith; "Virtual Worlds: No Interface to Design"; pp. 363–368; from *Cyberspace: First Steps*; edited by Michael Benedikt; 1991 (Seventh Printing: 1994); Massachusetts Institute of Technology; Cambridge, Massachusetts.

Carlson, A. L., et. al; "Development of a Binocular Visor Projection Helmet–Mounted Display"; pp. 131–134; from *SID International Symposium Digest of Technical Papers*; 1991; Society for Information Display; Playa del Rey, California.

Dickinson, Robert R.; "A Unified Approach to the Design of Visualization Software for the Analysis of Field Problems;" pp. 173–180; from *Three Dimensional Visualization and Display Technologies, Proceedings of the SPIE—The International Society of Optical Engineering*, edited by W. E. Robbins and S.S. Fisher; 1989; SPIE; Bellingham, Washington.

Dickinson, Robert R.; "Interactive 4–D Visualization of Fields"; pp. 1–10 text, and illustrations; from *Computer Science Technical Report CS–89–15*; 1989; Computer Graphics Laboratory, University Waterloo; Waterloo, Ontario, Canada.

Dickinson, R. R., et al.; "A Unified Approach to Interface Design for Data Visualization Using Desktop and Immersion Virtual Environments"; pp. 309–320; from *Virtual Reality Applications*; edited by R. A. Earnshaw, J. A. Vince, and H. Jones; 1995; Academic Press Limited; London, England and San Diego, California.

Eddings, Joshua; *How Virtual Reality Works*; pp. 19–32; 40–45; 53–55; 63; 65–67; 69–70; 72–73; 76–78; 84–85; 86–90; 98–103; 120–122; 124–125; 146–149; 1994; Ziff–Davis Press; Emeryville, CA 94608.

Fuchs, Henry; "Systems for Display of Three–Dimensional Medical Image Data"; pp. 315–331; from *3D Imaging in Medicine: Algorithms, Systems, Applications*; edited by Karl Heinz Hohne, Henry Fuchs, and Stephen M. Pizer; 1990; NATO Scientific Affairs Division and Springer–Verlag; Berlin, Germany.

Gilboa, Pini; Designing the Right Visor; pp. 154–163; from *Large–Screen Projection, Avionic, and Helmet–Mounted Displays, Proceedings of the SPIE—The International Society for Optical Engineering*, edited by H. M. Assenheim, Richard A. Flasck, Thomas M. Lippert, and Jerry Bentz; 1991; SPEI vol. 1456; San Jose, California.

Granieri, J. P., et. al; "Simulating Humans in Virtual Reality"; pp. 265–268; from *Virtual Reality Applications*; edited by R. A. Earnshaw, J. A. Vince, and H. Jones; 1995; Academic Press Limited; London, England and San Diego, California.

Grunwald, A., et. al.; "Visual Field Information in Nap–of–the–Earth Flight Teleoperated Helmet–Mounted Displays"; pp. 132–153; from *Large–Screen Projection, Avionic, and Helmet–Mounted Displays, Proceedings of the SPIE—The International Society for Optical Engineering*, edited by H. M. Assenheim, Richard A. Flasck, Thomas M. Lippert, and Jerry Bentz; 1991; SPEI vol. 1456; San Jose, California.

Harrington, David O.; "Normal Visual Field"; pp. 97–104; from *The Visual Fields: A Textbook and Atlas of Clinical Perimetry*; 1976; The C. V. Mosby Company; Saint Louis, Missouri.

Harrington, David O.; "Abnormal Visual Fields"; pp. 107–147; from *The Visual Fields: A Textbook and Atlas of Clinical Perimetry*; 1976; The C. V. Mosby Company; Saint Louis, Missouri.

Hendrix, C., et al.; "Presence within Virtual Environments as a Function of Visual Display Parameters"; pp. 274–289; from *Presence*, vol. 5, No. 3; Summer, 1996; Massachusetts Institute of Technology; Cambridge, Massachusetts.

Jaa–Aro, Kai–Mikael; "An Overview of Virtual Reality Research in the Nordic Countries"; pp. 138–167; from *The Virtual Reality Casebook*, edited by Carl Eugene Loeffler and Tim Anderson; 1994; Van Nostrand Reinhold; New York.

Jacobson, Robert; "Designing in Virtual Space"; pp. 243–249; from *The Virtual Reality Casebook*; 1994; edited by Carl Eugene Loeffler and Tim Anderson; 1994; Van Nostrand Reinhold; New York.

Kalawsky, Roy S.; *The Science of Virtual Reality and Virtual Environments*; pp. 1–16; 24–33; color plates; 43–69; 107–188; 210–220; 256–277; 315–319; 344; 347–355; 1993; Addison–Wesley Publishing Company; Workingham, England.

Kaufman, A., et. al; "Direct Interaction with a 3D Volumetric Environment"; pp. 33–34; *from Proceedings SIGGRAPH*; 1990; Copyright ACM; USA.

Kollin, J.; "A Retinal Display for Virtual–Environment Applications"; p. 887; from *SID International Symposium Digest of Technical Papers*; 1993; Society for Information Display; Playa del Rey, California.

Leigh, J., et. al.; "Virtual Reality in Computational Neuroscience"; pp. 293–294; 300–304; from *Virtual Reality Applications*; edited by R. A. Earnshaw, J. A. Vince, and H. Jones; 1995; Academic Press Limited; London, England and San Diego, California.

Loeffler, C. E., et. al.; "What is Virtual Reality?"; pp. xiii–xxv; from *The Virtual Reality Casebook*, edited by Carl Eugene Loeffler and Tim Anderson; 1994; Van Nostrand Reinhold; New York.

Massof, Robert W., et. al.; "Low Vision Enhancement System"; pp. 120–124; from *Johns Hopkins APL Technical Digest*; vol. 15, No. 2, 1994; Johns Hopkins University; Baltimore, Maryland.

Massof, Robert W.; "Low Vision Enhancement: Vision for the Future"; pp. 32–35; from *Eyecare Technology*, vol. 4, No. 1; Jan./Feb. 1994; Computers in EyeCare, Inc.; Folsom, California.

Penny, Simon; "Virtual Reality as the Completion of the Enlightenment"; pp. 199–200; from *The Virtual Reality Casebook*; 1994; edited by Carl Eugene Loeffler and Tim Anderson; 1994; Van Nostrand Reinhold; New York.

Peters, David L.; "Chasing the Eye: An Eye–Tracked Display for the Simulation Industry—The How and the Why"; pp. 495–497; from *SID International Symposium Digest of Technical Papers*; 1991; Society for Information Display; Playa del Rey, California.

Pimentel, K. et. al.; *Virtual Reality Through the New Looking Glass*; pp. xxi; 5–6; 8–12; 19–22; 65–71; 80–87; 94–106; 148–167; 201–202; 241–244; 279; 280–299; 359–370; 417; 1995; Intel/McGraw–Hill; New York.

Regan, E. C.; "Some Human Factors Issues in Immersive Virtual Reality: Fact and Speculation"; pp. 163–164; from *Virtual Reality Reality Applications*; edited by R. A. Earnshaw, J. A. Vince, and H. Jones; 1995; Academic Press Limited; London, England and San Diego, California.

Rheingold, Howard; *Virtual Reality*; pp. 113; 131–154; 215–255; 1991; Touchstone/Simon & Schuster; New York.

Satava, Richard M.; "Virtual Reality for the Physician of the 21st Century"; pp. 19–26; from *Virtual Reality Applications*; edited by R. A. Earnshaw, J. A. Vince, and H. Jones; 1995; Academic Press Limited; London, England and San Diego, California.

Sperlich, Tom; "We Continue Searching: Virtual Reality Research in Germany"; pp. 152–167; from *The Virtual Reality Casebook*; 1994; Van Nostrand Reinhold; New York.

Stone, Allucquere Rosanne; "Will the Real Body Please Stand Up?: Boundary Stories about Virtual Cultures"; pp. 95–99; from *Cyberspace: First Steps*; edited by Michael Benedikt; 1991 (Seventh Printing: 1994); Massachusetts Institute of Technology; Cambridge, Massachusetts.

Stuart, Rory; *The Design of Virtual Environments*; pp. 10; 13; 17–30; 45–47; 53–55; 60–61; 103–104; 114–117; 133–143; 1996; Mcgraw–Hill; New York.

Thalmann, Daniel; "Applications of Virtual Humans in Virtual Reality"; pp. 271–274; from *Virtual Reality Applications*; edited by R. A. Earnshaw, J. A. Vince, and H. Jones; 1995; Academic Press Limited; London, England and San Diego, California.

Traub, David C.; "The Promise of Virtual Reality for Learning"; pp. 107–117; from *The Virtual Reality Casebook*; 1994; edited by Carl Eugene Loeffler and Tim Anderson; 1994; Van Nostrand Reinhold; New York.

Wann, J. P., et. al.; "Natural Problems for Stereoscopic Depth Perception in Virtual Environments"; pp. 2731–2736; from *Vision Research*, 35(19); 1995; Elsevier Science Ltd.; Great Britain.

Webster, John A; "Stereoscopic Full Field of Vision Display System to Produce Total Visual Telepresence"; pp. 63–70; from *Display System Optics II, Proceedings of the SPIE—The International Society for Optical Engineering*, edited by H. M. Assenheim; 1989; SPEI vol. 1117; Orlando, Florida.

Wexelblat, Alan; "Giving Meaning to Place: Semantic Spaces"; pp. 257–271; from *Cyberspace: First Steps*; edited by Michael Benedikt; 1991 (Seventh Printing: 1994); Massachusetts Institute of Technology; Cambridge, Massachusetts.

Wodaski, Ron; *Virtual Reality Madness! 1996*; pp. 216–229; 588–590; 1995; Sams Publishing; Indianapolis, Indiana.

Yamaguchi, H., et. al.; "Proposal for A Large Visual Field Display Employing Eye Movement Tracking"; pp. 13–20; from *Optics, Illumination, and Image Sensing for Machine Vision IV, Proceedings of the SPIE—The International Society for Optical Engineering*; 1989; SPEI vol. 1194; Philadelphia, Pennsylvania.

VISUAL FIELD TESTING METHOD AND APPARATUS USING VIRTUAL REALITY

FIELD OF INVENTION

This invention relates to optical testing of the eye's sensitivity to various parameters of light, and in particular to visual field evaluation, using a Virtual Reality system.

DESCRIPTION RELATIVE TO THE PRIOR ART

In the field of medicine where disorders of the eye are treated, it is necessary to measure the sensitivity to light in various regions of the light-sensitive retina. So doing measures function, as well as quantifying disorders of the eye and the retina, the optic nerve, the optic chiasm, the visual pathways to the brain, and the brain itself. Visual field testing is mandatory for glaucoma diagnosis and treatment. Apparatus to measure the field of vision is used by ophthalmologists and optometrists for these purposes and is relatively complex in its various functions, some of which complexity tends to make the human patient become tired or lose attention to the test.

SUMMARY OF THE INVENTION

The purpose of the presently-described method and apparatus for visual field testing is to allow the sensitivity of the visual field to be measured without the attendant stress of the patient, and yet to preserve accuracy. The means by which this is accomplished uses concepts and apparatus from Virtual Reality. Virtual Reality is a term applied loosely to the experience of an individual when exposed to the appearance of surroundings which are presented by interactive apparatus for stimulation of the senses. The primary cues are usually visual, supplemented by audio, and the feedback to the apparatus is generally by physical movements of the individual experiencing the Virtual Reality (such as pressing a button or a switch, or speaking into a microphone).

The disclosed Virtual Reality visual field measuring method and apparatus uses a head-mounted goggle or face mask unit to present visual and audio stimuli to a patient. The visual portion has both relatively fixed image information, and superimposed visual areas, which may vary in time, place, color, and intensity. These stimuli are generated and controlled by software in an associated computer, which receives interactive feedback stimuli from the patient. Such stimuli include, but are not limited to, direction of gaze sensing, eyelid movement and blinking, audio, and hand pressure signals on cue.

Content of the software is dictated by the need to provide technically acceptable protocols. Such protocols provide for examining wide and narrow fields of view, selected areas, such as the blind spot or the fovea, and measurements of thresholds for sensitivity to light intensity, or, if desired, color. These are usually done for one eye at a time, each looking at the same, or similar, field of views.

Active feedback sensing alerts the system to patient loss of attention in general, or loss of fixation in particular, for notation and reiteration of test stimuli. In the presently-described method and apparatus, provision is also made for reiteration of individual test points when a result is found to be inconsistent with a predetermined norm, or when lack of concentration or poor cooperation becomes evident, with appropriate care taken to provide no leading cues which may cause false positive or false negative responses. The software allows optional restful imagery to be provided in the "background," in addition to a conventional, uniform featureless field. The imagery in various quadrants/areas may be patterns, or low-contract images, and may move quickly or slowly, and may have intensity, color, or temporal modulation. The intensity, color, location, and duration of the superimposed test points are displayed by conventional electronic means, such as are now used in image presentations. Such means include cathode-ray tube, electroluminescent, liquid crystal, and gas discharge panels. A hard-copy printout documenting patient responses is provided for the physician's records.

Another object of the present system is to provide relief from the stress of being required to concentrate, without head movement, one's gaze at a fixed location, as is the case with conventional visual field testers. The gaze sensor may be multi-element, so as to allow the gaze to be detected in a small solid angular range and, within this range, the effective fixation will be deemed to be maintained. The software may include an interest-fixation icon which encourages the gaze to trace its motion within the allowed solid angle, thus avoiding fixation fatigue. The software keeps track of the location of the test point frame of reference within that solid angle of displacement, so as to provide accurate mapping of test data on the field of view presented to the retina.

In addition to visual field testing, it is certainly within the scope of this invention to provide other Virtual Reality computer-driven, interactive testing capability, such as for visual acuity and color testing.

DESCRIPTION OF THE PREFERRED EMBODIMENT

Figure 2A:
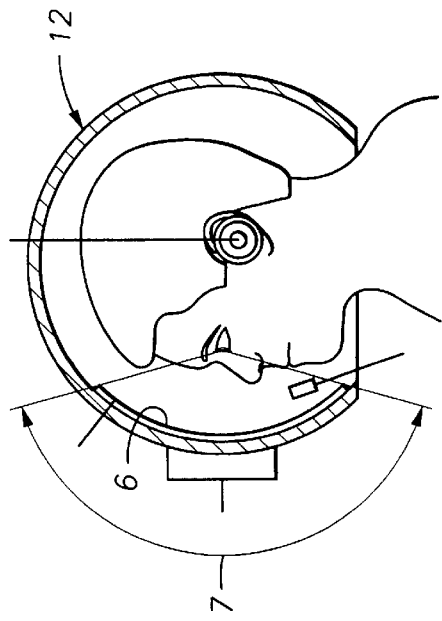
FIG. 2(a) shows, by dashed line 6, an image surface covering an angular field of view 7. Side View.
Figure 2B:
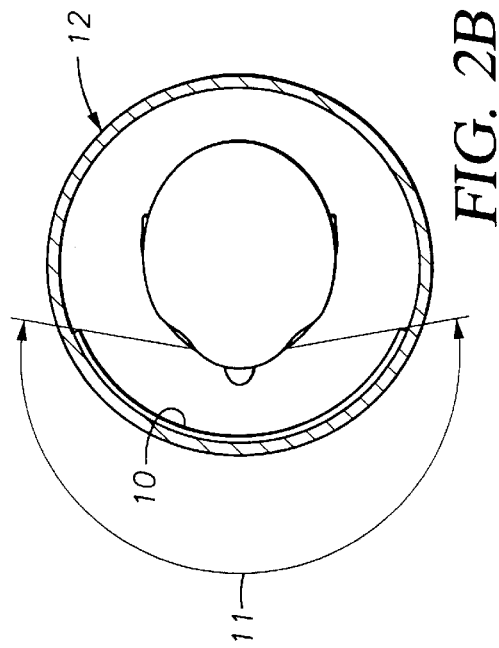
FIG. 2(b) shows, by dashed line 10, an image surface covering an angular field of view 11. Top view.
Figure 1:
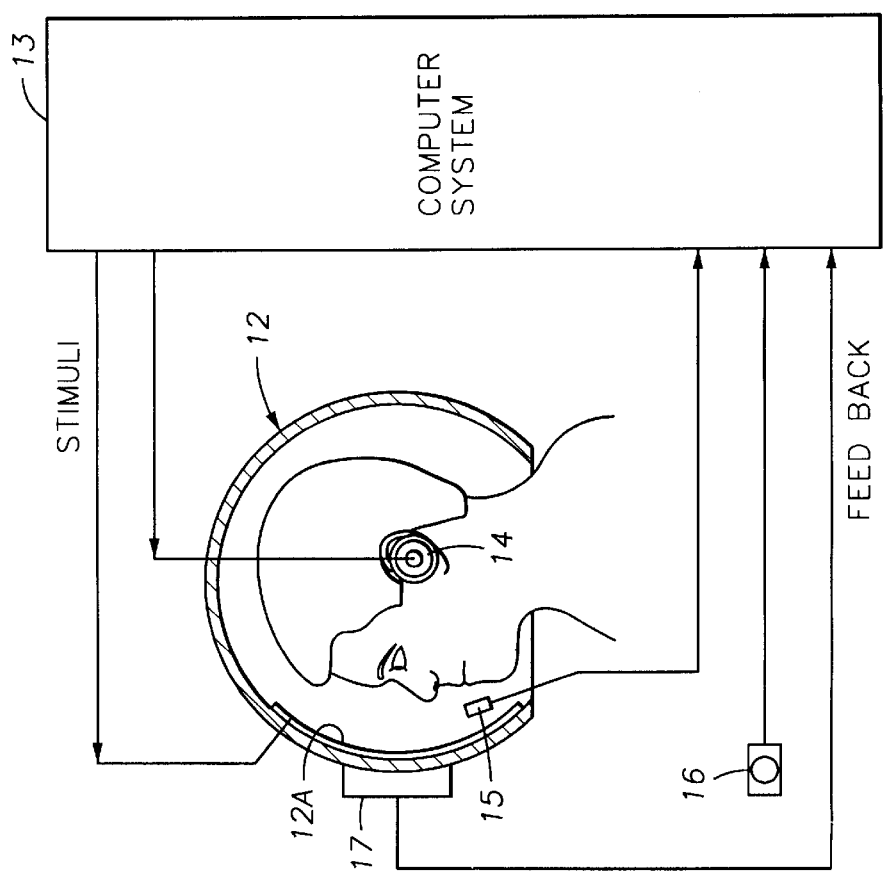
FIG. 1 shows a schematic in which head-gear 12, is connected to computer 13, which delivers visual signal to head-gear display screen 12(a), and audio signal to head-gear earphone 14. Microphone 15, provides feedback audio response to computer 13. Hand-actuated switch 16, provides feedback to computer 13, and gaze sensor 17, mounted in the direction of gaze, provides optical gaze direction feedback to computer 13.

A head-mounted visual display apparatus, which remains in a fixed spatial relationship to the patient's head during testing of the visual field, is adjustable to suit the individual patient, and is mounted on the patient's head by conventional means. A screen display is part of the head-gear and encompasses the maximum field of view required. The head-gear is provided with integral microphone and speaker, for audio communication and feedback, and a multi-element gaze-aim sensor array. This ensemble is connected, by appropriate means, to a computer which provides the necessary visual and audio stimuli for the patient, and which receives the feedback responses to enable interactive functioning of the system. A hand-operated switch is incorporated.

An element of the Virtual Reality testing system is that it allows the patient the freedom to shift his/her gaze, while in the test mode, without disruption of the process, thus relieving one of the causes of patient stress. Another feature provided is the ability to modulate the background scene brightness, contrast, color, optical stimulus size and detail, and duration of the test stimuli, all of which serve to relieve fatigue of the patient. Of paramount significance is that the patient may move around bodily, since the headgear is portable and, in addition, electrical interface to the computer may be wireless.

In addition to a vastly more patient-friendly and portable test setting, a further significant advantage of the presently-described method and apparatus is that background light intensity and other parameters can be easily calibrated to predetermined settings, thus eliminating the requirement mandated by conventional visual field testers to calibrate these parameters for the entire room. For instance, the fact that room brightness can vary almost imperceptibly, but yet significantly, from day to day in conventional visual field testing situations creates built-in unreliability of the test data received from the patient.

Furthermore, feelings of anxiety frequently displayed by patients undergoing conventional visual field testing in which first one eye and then the fellow eye is covered with an occluder patch can be eliminated in the preferred embodiment, since both eyes can be tested simultaneously, or separately and independently, through the use of individual eye goggles, or an appropriate face mask, to provide gaze separation.

The description above is by no means exhaustive of possible configurations, as well as other preferred embodiments, within the scope of the invention as an interactive Virtual Reality visual testing system.

We claim:

1. An apparatus using Virtual Reality for supplying, testing, measuring, and quantifying visual information to and from the visual pathways of the eye of a patient and the retina, the optic nerve, the optic chiasm, the visual pathways to the brain, and the brain, said apparatus comprising:
    a head-gear configuration placed on the head of the patient;
    an excitation device for applying test stimuli into said head-gear configuration;
    a feedback device for allowing the patient to respond to test stimuli;
    a sensing device for sensing feedback from the patient;
    a computer device for directing information to the excitation device and for receiving, interpreting, sequencing, and sending information to and from the patient;
    an electronic imaging system to display the sequenced presentation of said test stimali computer software and the result of interactive patient responses;
    a hard-copy printing device to supply a permanent record.

2. An apparatus as recited in claim 1, wherein said head-gear configuration consists of a face mask allowing the patient to observe a field of view into which test stimuli are presented to one eye at a time.

3. An apparatus as recited in claim 1, wherein said head-gear configuration consists of a face mask allowing the patient to observe a field of view in which test stimuli are presented to both eyes simultaneously.

4. An apparatus as recited in claim 1, wherein said head-gear configuration consists of goggles with independent eyepieces allowing the patient to observe a field of view into which test stimuli are presented to one eye at a time.

5. An apparatus as recited in claim 1, wherein said head-gear configuration consists of goggles with independent eyepieces allowing the patient to observe a field of view into which test stimuli are presented to both eyes simultaneously.

6. An apparatus as recited in claim 1, wherein said excitation device provides test stimuli which may be modified in placement within a field of view supplied to the patient.

7. An apparatus as recited in claim 1, wherein said excitation device provides test stimuli which may be modified in size within a field of view supplied to the patient.

8. An apparatus as recited in claim 1, wherein said excitation device provides test stimuli which may be modified in intensity of luminosity within a field of view supplied to the patient.

9. An apparatus as recited in claim 1, wherein said excitation device provides test stimuli which may be modified in duration of time within a field of view supplied to the patient.

10. An apparatus as recited in claim 1, wherein said excitation device provides test stimuli which may be modified in color within a field of view supplied to the patient.

11. An apparatus as recited in claim 1, wherein said excitation device provides test stimuli which may be modified in color intensity within a field of view supplied to the patient.

12. An apparatus as recited in claim 1, wherein said excitation device provides test stimuli in the form of letters for measuring visual acuity.

13. An apparatus as recited in claim 1, wherein said excitation device provides test stimuli in the form of symbols for measuring visual acuity.

14. An apparatus as recited in claim 1, wherein said excitation device provides test stimuli in the form of figures for measuring visual acuity.

15. An apparatus as recited in claim 1, wherein said excitation device provides an interest-fixation icon.

16. An apparatus as recited in claim 1, wherein the background for a field of view in which test stimuli are presented to the patient is uniform and featureless.

17. An apparatus as recited in claim 1, wherein the background for a field of view in which test stimuli are presented to the patient provides imagery consisting of patterns.

18. An apparatus as recited in claim 1, wherein the background for a field of view in which test stimuli are presented to the patient provides imagery which moves.

19. An apparatus as recited in claim 1, wherein the background for a field of view in which test stimuli are presented to the patient varies in contrast.

20. An apparatus as recited in claim 1, wherein the background for a field of view in which test stimuli are presented to the patient provides imagery which varies in intensity.

21. An apparatus as recited in claim 1, wherein the background for a field of view in which test stimuli are presented to the patient provides imagery which varies in color.

22. An apparatus as recited in claim 1, wherein the background for a field of view in which test stimuli are presented to the patient provides imagery which varies in duration.

23. An apparatus as recited in claim 1, wherein said feedback device consists of a button which the patient presses when stimuli are visually perceived.

24. An apparatus as recited in claim 1, wherein said feedback device consists of a switch which the patient presses when stimuli are visually perceived.

25. An apparatus as recited in claim 1, wherein said feedback device consists of a microphone into which the patient speaks when stimuli are visually perceived.

26. An apparatus as recited in claim 1, wherein said sensing device recognizes direction of gaze sensation of the patient.

27. An apparatus as recited in claim 1, wherein said sensing device recognizes eyelid movement and blinking of the patient.

28. An apparatus as recited in claim 1, wherein said sensing device recognizes direction of gaze of the patient.

29. An apparatus as recited in claim 1, wherein said sensing device recognizes eyelid movement and blinking of the patient.

30. An apparatus as recited in claim 1, wherein said sensing device recognizes fatigue and inattention of the patient.

31. An apparatus as recited in claim 1, wherein said sensing device recognizes poor cooperation of the patient.

32. An apparatus as recited in claim 1, wherein said sensing device is single-element.

33. An apparatus as recited in claim 1, wherein said sensing device is multi-element.

34. An apparatus as recited in claim 1, wherein said computer device utilizes predetermined software programs for providing commands to the excitation device for sequenced presentation of test stimuli to the patient.

35. An apparatus as recited in claim 1, wherein said computer device provides commands to the excitation device to provide a uniform featureless field.

36. An apparatus as recited in claim 1, wherein said computer device provides commands to the excitation device to provide background imagery.

37. An apparatus as recited in claim 1, wherein said computer device correlates and interprets information received from the feedback device.

38. An apparatus as recited in claim 1, wherein said computer device provides reiterated commands to the excitation device of appropriately-modulated test stimuli for repeat presentation to the patient.

39. An apparatus as recited in claim 1, wherein said computer comprises:
software to track the location of the test stimuli frame of reference in relation to a fixation of the patient;
software to shift spatially said frame of reference so as to maintain accurate mapping of the test stimuli data on a field of view presented to the retina.

40. An apparatus as recited in claim 1, wherein said computer device provides software to measure and quantify the peripheral field of vision of the patient.

41. An apparatus as recited in claim 1, wherein said computer device provides software to measure and quantify color vision of the patient.

42. An apparatus as recited in claim 1, wherein said computer device provides software to measure and quantify the visual acuity of the patient.

43. An apparatus as recited in claim 1, wherein said computer device provides ongoing directions to the patient through either audio or visual commands.

44. An apparatus as recited in claim 1, wherein said electronic imaging system is a cathode-ray tube display panel.

45. An apparatus as recited in claim 1, wherein said electronic imaging system is an electroluminescent display panel.

46. An apparatus as recited in claim 1, wherein said electronic imaging system is a liquid crystal display panel.

47. An apparatus as recited in claim 1, wherein said electronic imaging system is a gas-discharge display panel.

48. A method using Virtual Reality for supplying, testing, measuring, and quantifying visual information to and from the visual pathways of the eye of a patient and the retina, the optic nerve, the optic chiasm, the visual pathways to the brain, and the brain, said method comprising:
providing a head-gear configuration placed on the head of the patient;
providing an excitation device for applying test stimuli into said head-gear configuration;
providing a feedback device for allowing the patient to respond to test stimuli;
providing a sensing device for sensing feedback from the patient;
providing a computer device for directing information to the excitation device and for receiving, interpreting, sequencing, and sending information to and from the patient;
providing an electronic imaging system to display the sequenced presentation of said test stimuli and the result of interactive patient responses;
providing a hard-copy printing device to supply a permanent record.

49. A method as recited in claim 48, wherein said head-gear configuration provides a face mask allowing the patient to observe a field of view into which test stimuli are presented to one eye at a time.

50. A method as recited in claim 48, wherein said head-gear configuration provides of a face mask allowing the patient to observe a field of view into which test stimuli are presented to both eyes simultaneously.

51. A method as recited in claim 48, wherein said head-gear configuration provides goggles with independent eyepieces allowing the patient to observe a field of view in which test stimuli are presented to one eye at a time.

52. A method as recited in claim 48, wherein said head-gear configuration provides goggles with independent eyepieces allowing the patient to observe a field of view into which test stimuli are presented to both eyes simultaneously.

53. A method as recited in claim 48, wherein said excitation device provides test stimuli which may be modified in placement within a field of view supplied to the patient.

54. A method as recited in claim 48, wherein said excitation device provides test stimuli which may be modified in size within a field of view supplied to the patient.

55. A method as recited in claim 48, wherein said excitation device provides test stimuli which may be modified in intensity of luminosity within a field of view supplied to the patient.

56. A method as recited in claim 48, wherein said excitation device provides test stimuli which may be modified in duration of time within a field of view supplied to the patient.

57. A method as recited in claim 48, wherein said excitation device provides test stimuli which may be modified in color within a field of view supplied to the patient.

58. A method as recited in claim 48, wherein said excitation device provides test stimuli which may be modified in color intensity within a field of view supplied to the patient.

59. A method as recited in claim 48, wherein said excitation device provides test stimuli in the form of letters for measuring visual acuity.

60. A method as recited in claim 48, wherein said excitation device provides test stimuli in the form of symbols for measuring visual acuity.

61. A method as recited in claim 48, wherein said excitation device provides test stimuli in the form of figures for measuring visual acuity.

62. A method as recited in claim 48, wherein said excitation device provides an interest-fixation icon.

63. A method as recited in claim 48, wherein the background for a the field of view in which test stimuli are presented to the patient is uniform and featureless.

64. A method as recited in claim 48, wherein the background for a field of view in which test stimuli are presented to the patient provides imagery consisting of patterns.

65. A method as recited in claim 48, wherein the background for a field of view in which test stimuli are presented to the patient provides imagery which moves.

66. A method as recited in claim 48, wherein the background for a field of view in which test stimuli are presented to the patient varies in contrast.

67. A method as recited in claim 48, wherein the background for a field of view in which test stimuli are presented to the patient provides imagery which varies in intensity.

68. A method as recited in claim 48, wherein the background for a field of view in which test stimuli are presented to the patient provides imagery which varies in color.

69. A method as recited in claim 48, wherein the background for a field of view in which test stimuli are presented to the patient provides imagery which varies in duration.

70. A method as recited in claim 48, wherein the feedback device consists of a button which the patient presses when stimuli are visually perceived.

71. A method as recited in claim 48, wherein said feedback device consists of a switch which the patient presses when stimuli are visually perceived.

72. A method as recited in claim 48, wherein said feedback device consists of a microphone into which the patient speaks when stimuli are visually perceived.

73. A method as recited in claim 48, wherein said sensing device recognizes direction of gaze sensation of the patient.

74. A method as recited in claim 48, wherein said sensing device recognizes eyelid movement and blinking of the patient.

75. A method as recited in claim 48, wherein said sensing device recognizes direction of gaze of the patient.

76. A method as recited in claim 48, wherein said sensing device recognizes eyelid movement and blinking of the patient.

77. A method as recited in claim 48, wherein said sensing device recognizes fatigue and inattention of the patient.

78. A method as recited in claim 48, wherein said sensing device recognizes poor cooperation of the patient.

79. A method as recited in claim 48, wherein said sensing device is single-element.

80. A method as recited in claim 48, wherein said sensing device is multi-element.

81. A method as recited in claim 48, wherein said computer device utilizes predetermined software programs for providing commands to the excitation device for sequenced presentation of test stimuli to the patient.

82. A method as recited in claim 48, wherein said computer device provides commands to the excitation device to provide a uniform featureless field.

83. A method as recited in claim 48, wherein said computer device provides commands to the excitation device to provide background imagery which can be varied.

84. A method as recited in claim 48, wherein said computer device correlates and interprets information received from the feedback device.

85. A method as recited in claim 48, wherein said computer device provides reiterated commands to the excitation device of appropriately-modulated test stimuli for repeat presentation to the patient.

86. A method as recited in claim 48, wherein said computer comprises:

software to track the location of the test stimuli frame of reference in relation to a fixation of the patient;

software to shift spatially said frame of reference so as to maintain accurate mapping of the test stimuli on a field of view presented to the retina.

87. A method as recited in claim 48, wherein said computer device provides software to measure and quantify the peripheral field of vision of the patient.

88. A method as recited in claim 48, wherein said computer device provides software to measure and quantify color vision of the patient.

89. A method as recited in claim 48, wherein said computer device provides software to measure and quantify the visual acuity of the patient.

90. A method as recited in claim 48, wherein said computer device provides ongoing directions to the patient through either audio or visual commands.

91. A method as recited in claim 48, wherein said electronic imaging system is a cathode-ray tube display panel.

92. A method as recited in claim 48, wherein said electronic imaging system is an electroluminescent display panel.

93. A method as recited in claim 48, wherein said electronic imaging system is a liquid crystal display panel.

94. A method as recited in claim 48, wherein said electronic imaging system is a gas-discharge display panel.

* * * * *